United States Patent [19]

McGill

[11] 4,177,349

[45] Dec. 4, 1979

[54] SUBSTITUTED 2,2'-BIPYRIDYL COMPOUNDS AND PROCESS FOR PREPARING SAME

[75] Inventor: Charles K. McGill, Indianapolis, Ind.

[73] Assignee: Reilly Tar & Chemical Corporation, Indianapolis, Ind.

[21] Appl. No.: 928,396

[22] Filed: Jul. 27, 1978

[51] Int. Cl.$^2$ .......................................... C07D 213/22
[52] U.S. Cl. .................................... 546/255; 546/256
[58] Field of Search ................................ 546/255, 256

[56] References Cited

PUBLICATIONS

Rosevear et al., J. Heterocyclic Chem., vol. 8, issue 3, pp. 483–485, (1971).
Sasse et al., J. Chem. Soc., pp. 1347–1350, (1961).
Badger et al., J. Chem. Soc., pp. 616–620, (1956).
Case et al., J. Am. Chem. Soc., vol. 78, pp. 5842–5844, (1956).

*Primary Examiner*—Alan L. Rotman
*Attorney, Agent, or Firm*—Woodard, Weikart, Emhardt & Naughton

[57] ABSTRACT

A process for preparing substituted 2,2'-bipyridyl compounds and several compounds so prepared, the process comprising the steps of first selecting a substituted pyridine of the formula defined herein, then mixing a stoichiometric excess of the substituted pyridine with an amount of sodamide, causing the resultant mixture to be at a temperature sufficiently high to cause substituted 2,2'-bipyridyl formation, and isolating the substituted 2,2'-bipyridyl thereby formed. The new substituted 2,2'-bipyridyl compounds are selected from the group consisting of 4,4'-di-(5-nonyl)-2,2'-bipyridyl; 4,4'-di-(3-pentyl)-2,2'-bipyridyl; 6,6'-di-(3-pentyl)-2,2'-bipyridyl; 6,6'-di-(5-nonyl)-2,2'-bipyridyl; 4,4'-di-(cyclohexylmethyl)-2,2'-bipyridyl; 5,5'-di-(5-nonyl)-2,2'-bipyridyl; 4,4'-di-(3-phenylpropyl)-2,2'-bipyridyl; 4,4'-di-(4-tetrahydropyranyl)-2,2'-bipyridyl; 4,4'-di-benzyl-2,2'-bipyridyl; 6,6'-di-isoamyl-2,2'-bipyridyl; and 4,4'-di-(t-butyl)-2,2'-bipyridyl.

18 Claims, No Drawings

SUBSTITUTED 2,2'-BIPYRIDYL COMPOUNDS AND PROCESS FOR PREPARING SAME

BACKGROUND OF THE INVENTION

This invention relates to bipyridyl compounds, and particularly, to several new substituted 2,2'-bipyridyl compounds and a process for preparing the same.

Pyridine, recognized by its characteristic $C_5H_5N$ formula, has been known for many years and is the parent ring system of a large number of naturally occurring products and important industrial, pharmaceutical and agricultural chemicals. It is an aromatic compound and, much like benzene, gives rise to a large number of substituted homologs and derivatives, many of which are found in the light- and middle-oil fractions of coal tar and are commonly known as pyridine bases.

Bipyridyls, generally categorized by their 2,2'-, 3,3'- and 4,4'-connections, are one such group of pyridine homologs and derivatives and have themselves been generally known to the art for many years. Various of the substituted bipyridyl compounds have long been available and recognized at least in recent years as valuable chelating agents for a variety of metal ions, an example being an article by P. E. Rosevear and W. H. F. Sasse entitled "The Synthesis of Some 4,4',4''-trialkyl-2,2':6',2''-terpyridyls (1,2)" appearing in *The Journal of Heterocyclic Chemistry*, vol. 8, issue 3, pages 483-5 (1971).

The preparation of such prior art bipyridyl compounds has been accomplished by one of several methods, the most common being refluxing pyridine in the presence of various catalytic agents. One such recognized and useful catalyst for the preparation of bipyridyl compounds from pyridine and its substituted derivatives is generally identified as Raney nickel. References to such catalytic reactions can be found in articles entitled: (1) "Synthetic Applications of Activated Metal Catalysts. Part XII. The Preparation of Symmetrically Substituted 2,2' Bipyridyls." by W. H. F. Sasse and C. P. Wittle, appearing in the *J. Chem. Soc.*, pages 1347-50 (1961); and (2) "Synthetic Applications of Activated Metal Catalysts. Part II. The Formation of Heterocyclic Diaryls." by G. M. Badger and W. H. F. Sasse, appearing in the *J. Chem. Soc.*, pages 616-20 (1956). A second recognized catalyst for accomplishing such bipyridyl formation is a palladium-on-carbon catalyst, commonly referred to as Pd/C. Reference to such Pd/C catalytic reactions can also be found in the 1971 article listed above in *The Journal of Heterocyclic Chemistry*.

Major problems, however, are encountered when working with these catalytic agents. First, the initial cost of such agents is often prohibitively high. Second, the reaction times are substantially long thus adding to the overall cost in both time and money of the bipyridyl preparations. Third, after a certain period of use, these catalytic agents become spent and must be reactivated often at significant expense in terms of both money and lost preparation time.

A second possible prior art method for the preparation of substituted bipyridyl compounds is generally referred to as the Ullmann reaction, as mentioned briefly in a 1956 article entitled "The Preparation of Some Substituted 2,6-Bis-(2-pyridyl)-pyridines" by F. H. Case and T. J. Casper, appearing in *J. Am. Chem. Soc.*, vol. 78, pages 5842-4 (1956). Specifically, the Ullmann reaction consists of several steps. The first step includes forming substituted 2-bromopyridine by reacting substituted 2-aminopyridine in the presence of sodium nitrite and hydrogen bromide. The second step includes forming the substituted 2,2'-bipyridyl by heating the substituted 2-bromopyridine with a copper or copper bronze powder. The third step includes separating the desired end product.

The Ullmann reaction, however, is not desirable or suitable for effective bipyridyl formation because it requires three distinct steps and even then, only results in low yields. After first obtaining the 2-aminopyridine, it has to be reacted in an involved and controlled two-step process just to form the bipyridyl compound. Then, isolation and recovery of the bipyridyl product is often complicated and costly.

It has also long been known that some coupling, i.e., bipyridyl formation, occurs as one of several side reactions that takes place in the amination process of pyridine and its substituted derivatives. Specifically, amination is generally achieved by means of the long-accepted Tschitschibabin reaction in which pyridine, or one of its alkyl derivatives, is heated with an amount of sodamide in the presence of boiling toluene or an appropriate dialkylaniline. The main product of the amination process is 2-aminopyridine, or a substituted 2-aminopyridine, as spelled out in *Leffler, Organic Reactions*, vol. I, chapter 4 (1942), entitled "Amination of Heterocyclic Bases by Alkali Amides."

In his work, Leffler specifically discusses the side coupling reaction on pages 95 and 96 in vol. I, Chap. 4, stating that "[b]ipyridyls are also produced in the preparation of aminopyridine." He further states that such side reaction products are often formed in significant quantities when hydrocarbon solvents are employed and that they may undergo amination if the conditions of reaction are sufficiently strenuous, particularly if in the presence of boiling xylene. In this regard, "significant quantities" is not defined or referenced in Leffler's work; but it is apparent from Leffler's treatment that the bipyridyl formed remains merely a byproduct produced in one of various side reactions that take place during the primary amination process.

In an article entitled "Amination in the Heterocyclic Series by Sodium Amide" by R. Norris Shreve, E. H. Riechers, Harry Rubenkoenig and A. H. Goodman, *Ind. Eng. Chem.*, 32, 173 (1940), cited as a reference in Leffler's treatise, 4,4'-dipyridyl is disclosed as only one of a few other nitrogen-containing compounds which were isolated from the diaminopyridine mother liquor. In this context, "dipyridyl" and "bipyridyl" are equivalent terms for all practical purposes and shall be treated as such for the remainder of the present application.

Another reference in Leffler is F. W. Bergstrom and W. Conard Fernelius, *Chem. Rev.*, 12, 156 (1933), which states only that a "large excess of pyridine," when combined with potassium amide at room temperature, "results in the formation, in poor yield, of a soluble blue-colored mono-potassium salt of a partly reduced 4,4'-dipyridyl" with "[v]ery little or no [formation of] 2-aminopyridine . . . "

From analysis of the above prior art references cited by Leffler, it is reasonable to conclude that Leffler's "significant quantities" of bipyridyl formation during the amination of pyridine and its substituted alkylpyridine derivatives, in the presence of either sodium or potassium amide, remain "in poor yield" as shown by F. W. Bergstrom and W. Conard Fernelius, even when large excesses of pyridine or its derivatives are reacted. This prior art amination process was thus known to be an ineffective and impractical method for producing high yields of bipyridyl compounds. Moreover, such processes often present major difficulties in separation and recovery of the small amount of desired bipyridyl from the reaction mixture.

Therefore, as evidenced by the various prior art references discussed herein, of the several methods for forming such bipyridyl compounds known to the art, no known method or process provides an efficient and practical way to prepare effective and substantial yields of these bipyridyls suitable for commercial application.

SUMMARY OF THE INVENTION

One embodiment of the present invention comprises a process for preparing a substituted 2,2'-bipyridyl compound including the first step of selecting a substituted pyridine of the formula

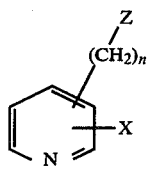

wherein:
(1) X is hydrogen or an alkyl group having from 1 to about 9 carbon atoms;
(2) Z is:
 (i) a branched chain alkyl group having from 3 to about 20 carbon atoms connecting to $(CH_2)_n$ at a point of branching when n=0, 1, 2; or
 (ii) a cyclic structure of the type

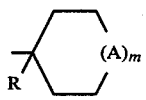

when n=0, 1, 2, wherein
 (a) A is methylene, oxygen, or sulfur when m=0, 1; and
 (b) R is hyrdogen or an alkyl group having from 1 to about 4 carbon atoms; or
 (iii) a phenyl group when n=1, 2, 3,; and
(3) the 2- or 6-position is occupied by hydrogen. The process includes the further steps of then mixing a stoichiometric excess of the selected substituted pyridine with an amount of sodamide, the mixing being in a mole ratio of at least about 2:1, causing the resultant mixture to be at a temperature sufficiently high to cause substituted 2,2'-bipyridyl formation and isolating the substituted 2,2'-bipyridyl formed during the causing.

The above embodiment of the present invention provides a significantly improved process for preparing effective yields of substituted 2,2'-bipyridyl compounds and is a marked advance over known prior art processes in this regard. Similar in some respects to the long-known amination process for pyridine, as discussed above, the present process has shown unexpected and surprising success in achieving significantly high bipyridyl yields far in excess of the express statements and expectations of the prior art. The high yields of these 2,2'-bipyridyls are further accompanied by minimal, and in most cases no, production of any corresponding substituted 2-aminopyridines. The substituted 2,2'-bipyridyls are thus produced in high yields and are the main product of the reaction in direct contradiction to the prior art teachings by Leffler, Bergstrom and Fernelius, and Shreve et al.

In one mode of practicing the above embodiment, the mixing of substituted pyridine with sodamide is in the ratio of about at least 3:1 with the causing step being to a temperature of between about 140° C. and about 220° C. and for a period of time sufficient to provide a bipyridyl yield of at least about 50 percent. This mixing may be further done with or without the presence of a hydrocarbon solvent. In this mode and with the period being at least about 3 hours, substituted 2-aminopyridine production is effectively eliminated and significant yields of substituted 2,2'-bipyridyls are achieved thereby marking a major advance over prior art processes. The unreacted substituted pyridine in the reaction is also recycled thereby eliminating any waste and more efficiently and marketably producing the 2,2'-bipyridyl compounds.

A second embodiment of the present invention comprises a substituted 2,2'-bipyridyl compound selected from the group consisting of 4,4'-di-(5-nonyl)-2,2'-bipyridyl; 4,4'-di-(3-pentyl)-2,2'-bipyridyl; 6,6'-di-(3-pentyl)-2,2'-bipyridyl; 6,6'-di-(5-nonyl)-2,2'-bipyridyl; 4,4'-di-(cyclohexylmethyl)-2,2'-bipyridyl; 5,5'-di-(5-nonyl)-2,2'-bipyridyl; 4,4'-di-(3-phenylpropyl)-2,2'-bipyridyl; 4,4'-di-(4-tetrahydropryranyl)-2,2'-bipyridyl; 4,4'-di-benzyl-2,2'-bipyridyl; 6,6'-di-isoamyl-2,2'-bipyridyl; and 4,4'-di-(t-butyl)-2,2'-bipyridyl.

The individual compounds comprising this embodiment of the present invention have not previously been known or prepared to applicant's knowledge and such compounds exhibit significant and valuable properties as chelating agents for various metal ions. They also exhibit significant and valuable properties as fungicides.

One object of the present invention is to provide an improved process for preparing substituted 2,2'-bipyridyl compounds in which substantial and effective yields of such bipyridyls are achieved as the main product of the process without any need for expensive catalytic agents.

Another object of the present invention is to provide an improved process for the preparation of substituted 2,2'-bipyridyl compounds in which substantial and effective yields of such bipyridyls are achieved without the significant side production of any other compounds such as the corresponding substituted 2-aminopyridines.

Another object of the present invention is to provide an improved process for the preparation of substituted 2,2'-bipyridyl compounds in which the prior art amination process is effectively altered and changed to produce substantially high yields of the bipyridyl compounds with minimal or no production of the corresponding substituted 2-aminopyridines.

Another object of the present invention is to provide several new substituted 2,2'-bipyridyl compounds which are unknown to the art and have significant and valuable properties as chelating agents for various metal ions and as fungicides.

Related objects and advantages of the present invention will be apparent from the following description.

DESCRIPTION OF THE PREFERRED EMBODIMENT

In accordance with the above discussion, one embodiment of the present invention comprises a process for preparing a substituted 2,2'-bipyridyl compound including the first step of selecting a substituted pyridine of the formula

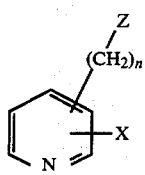

wherein:
(1) X is hydrogen or an alkyl group having from 1 to about 9 carbon atoms;
(2) Z is:
(i) a branched chain alkyl group having from 3 to about 20 carbon atoms connecting to $(CH_2)_n$ at a point of branching when n=0, 1, 2; or
(ii) a cyclic structure of the type

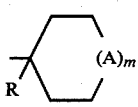

when n=0, 1, 2, wherein
(a) A is methylene, oxygen, or sulfur when m=0, 1; and
(b) R is hyrdogen or an alkyl group having from 1 to about 4 carbon atoms; or
(iii) a phenyl group when n=1, 2, 3,; and
(3) the 2- or 6-position is occupied by hydrogen.

An example of such a substituted pyridine suitable for selection and use in the present process is 4-(5-nonyl)-pyridine, and the same will be periodically referred to throughout the remainder of the specification whenever necessary to specifically and concisely describe an example of this embodiment of the present invention. In this same regard, testing to date has shown the pyridine compounds most practical and suitable for use in the process of the present invention have up to about 20 carbon atoms in their branched alkyl chains with the most preferred compounds exhibiting a branched chain of between about 5 and about 10 carbon atoms.

The next step in the process is mixing a stoichiometric excess of this substituted pyridine with an amount of sodamide, which has the general formula $NaNH_2$. This mixing may be done with or without the presence of a hydrocarbon solvent such as xylene. Through experimentation, it was found that such mixing must be in a mole ratio of at least about 2:1 substituted pyridine to sodamide in order to produce high yields of the corresponding 2,2'-bipyridyl while also minimizing side production of the substituted 2-aminopyridine. Experimentation has also shown that for those tested substituted pyridines of the general formula defined above, the mixing must be in a mole ratio of at least about 3:1 in order to guarantee maximum production and yield of the substituted 2,2'-bipyridyl while also eliminating any measurable side production of the corresponding substituted 2-aminopyridine.

The resultant mixture of substituted pyridine and sodamide is then caused to be at a temperature sufficiently high to cause substituted 2,2'-bipyridyl formation. The appropriate temperature for promoting this 2,2'-bipyridyl formation varies greatly, of course, according to the specific substituted pyridine selected and the exact mole ratio, pressure and other factors existing during the reaction. However, testing to date, as further set forth below, has shown that a temperature of between about 140° C. and about 220° C. is required in order to cause formation of the substituted 2,2'-bipyridyl compounds.

For practicable and marketable application of the present process, the resultant mixture must be kept at this elevated temperature for a period of time sufficient to provide a yield of at least about 50 percent 2,2'-bipyridyl based on the amount of substituted pyridine consumed. Although this "period of time" varies greatly according to the particular components and conditions present, the above-mentioned experimentation has further shown that refluxing the mixture at the elevated temperature for a period of at least about 3 hours is required to produce significant yields of the 2,2'-bipyridyl compounds. In addition, with certain substituted alkylpyridine compounds, testing has shown that maintaining the refluxing mixture at the elevated temperature for periods up to and exceeding 26 hours is not detrimental and, on the contrary, results in more efficient and higher yields of the 2,2'-bipyridyl compounds while minimizing or even eliminating 2-aminopyridine production.

The final step in the improved process of the present invention is to isolate the substituted 2,2'-bipyridyl formed during the causing step. To accomplish this, various known methods can, of course, be used and such are clearly within the contemplation and scope of the present invention. However, in this embodiment, this isolating is accomplished by first allowing the reacted mixture to cool. The mixture is then hydrolyzed with an amount of water and a distilling operation is used to recover both the unreacted substituted pyridine and the substituted 2,2'-bipyridyl produced during the process, as well as any corresponding substituted 2-aminopyridine formed as a side product in the reaction. Any unreacted substituted pyridine thereby recovered is then recycled for use in subsequent 2,2'-bipyridyl formation.

As previously discussed, a second embodiment of the present invention comprises a new substituted 2,2'-bipyridyl compound selected from the group consisting of:

4,4'-di-(5-nonyl)-2,2'-bipyridyl;
4,4'-di-(3-pentyl)-2,2'-bipyridyl;
6,6'-di-(3-pentyl)-2,2'-bipyridyl;
6,6'-di-(5-nonyl)-2,2'-bipyridyl;
4,4'-di-(cyclohexylmethyl)-2,2'-bipyridyl;
5,5'-di-(5-nonyl)-2,2'-bipyridyl;
4,4'-di-(3-phenylpropyl)-2,2'-bipyridyl;
4,4'-di-(4-tetrahydropyranyl)-2,2'-bipyridyl;
4,4'-di-benzyl-2,2'-bipyridyl;
6,6'-di-isoamyl-2,2'-bipyridyl; and
4,4'-di-(t-butyl)-2,2'-bipyridyl.

These compounds were prepared using the above-described improved process of the present invention and each one exhibits significant and valuable properties as a chelating agent for various metal ions such as copper and iron. Testing has shown the compounds also exhibit significant fungicidal and bactericidal properties and would be useful for preparing pickling inhibitors for various in-line pickling processes.

For the purposes of promoting a better understanding of the improved process and individual compounds of the present invention, reference will now be made to specific examples of the preparation and use of such substituted 2,2'-bipyridyl compounds using the improved process as above described. Specifically, Table I depicts 7 separate experiments which were conducted using various mole ratios and reaction conditions for the preparation of 4,4'-di-(5-nonyl)-2,2'-bipyridyl from the combination of 4-(5-nonyl)pyridine and sodamide. Of these experiments, numbers 2 and 6 are described in detail below with similar procedures having been followed for the other numbered experiments. Table II contains experimental data for the preparation of the other 10 substituted 2,2'-bipyridyl compounds listed above and for a previously-known 4,4'-di-(isopropyl)-2,2'-bipyridyl compound, such preparations having followed similar procedures to those specifically set out below for the 4,4'-di-(5-nonyl)-2,2'-bipyridyl and various other of the compounds. Infrared and nuclear magnetic resonance (nmr) spectra were used for structural identification.

EXAMPLE 1

Experiment No. 2

4,4'-di-(5-nonyl)-2,2'-bipyridyl

Liquid ammonia, containing one mole of freshly prepared sodamide, was replaced with 500 cc of N,N-dimethylaniline. The mixture was heated to 150° C. and 102.5 g (0.5 moles) of 4-(5-nonyl)pyridine was rapidly added through a dropping funnel. This mixture was heated to 175° C. at which point a fast evolution of hydrogen gas began. The reaction mixture was kept at 175°-180° C. for 4.5 hours and then allowed to cool over night with little hydrogen gas evolution during the last hour of the heating period. The cooled mixture was then hydrolyzed with 200 cc of water and the organic phase was separated and distilled to give 8.7 g of unreacted 4-(5-nonyl)pyridine and 39.2 g of 2-amino-4-(5-nonyl)pyridine, with most of the aminopyridine product boiling at 162°-164° C. and 2 mm Hg. Also obtained from such distilling was 18.6 g of 4,4'-di-(5-nonyl)-2,2'-bipyridyl, such 2,2'-bipyridyl product boiling at 237°-250° C. and 1 mm Hg. Based on the recovered 4-(5-nonyl)pyridine, yields were calculated for the amino product of 38.9% and for the 2,2'-bipyridyl product of 19.9%. Upon subsequent testing, the 2,2'-bipyridyl product performed effectively as a metal chelating agent and exhibited significant and valuable fungicidal properties.

EXAMPLE 2

Experiment No. 6

4,4'-di-(5-nonyl)-2,2'-bipyridyl

To a boiling mixture of 0.3 moles of sodamide and 500 cc of xylene was added 200 g (0.98 moles) of 4-(5-nonyl)pyridine. The mixture was refluxed at 146°-147° C. for 6 hours and then allowed to cool before hydrolyzing with 100 cc of water. The xylene layer was then distilled to recover 138.2 g of unreacted 4-(5-nonyl)pyridine and 50.0 g of 4,4'-di-(5-nonyl)-2,2'-bipyridyl boiling at 224°-227° C. and 0.4 mm Hg. The effective yield of the 2,2'-bipyridyl product was 81.3%, based on the recovered 4-(5-nonyl)pyridine, with no side production of the amino byproduct.

EXAMPLE 3

Experiment No. 8

6,6'-di-(5-nonyl)-2,2'-bipyridyl

In a two-liter, three-neck flask, equipped with a stirrer and dropping funnel, was prepared 0.20 mole of sodamide, using an iron catalyst, in about 600 cc of liquid ammonia. The ammonia was replaced by adding 1,000 g of N,N-dimethylaniline through the dropping funnel and evaporating the ammonia. A thermometer and reflux condenser were added to the flask. The mixture was heated to 152° C. and 205 g (1.0 mole) of 2-(5-nonyl)pyridine was added. No reaction took place. The mixture was slowly heated to 197° C. when hydrogen evolution started, and the reaction mixture turned purple. The reaction continued at 197°-198° C. for 3 hours, at which time the hydrogen evolution became slow. The reaction mixture was cooled to about room temperature and hydrolyzed with 200 cc of water. The oil layer was separated and distilled to give 125 g (0.61 mole) of unreacted 2-(5-nonyl)pyridine, 2.3 g (0.01 mole) of 2-amino-(5-nonyl)pyridine (2.7% yield) and 35.8 g (0.09 mole) of 6,6'-di-(5-nonyl)-2,2'-bipyridyl boiling at 251°-259° C. and 7 mm Hg. The yield of 2,2'-bipyridyl product based on recovered 2-(5-nonyl)pyridine was 45.0%.

EXAMPLE 4

Experiment No. 14

4,4'-di-(cyclohexylmethyl)-2,2'-bipyridyl

In a one-liter, three-neck flask was prepared 0.1 mole of sodamide (from 2.3 g of sodium) in about 500 cc of liquid ammonia. The ammonia was replaced with 200 cc of xylene. The xylene and sodamide mixture was brought to reflux and 103.3 g (0.59 mole) of 4-cyclohexylmethylpyridine was added. The reaction mixture was refluxed at 128°-148° C. for 3.5 hours, during which time it turned a dark purple and hydrogen was evolved.

The mixture was then cooled to room temperature and hydrolyzed with 50 cc of water. The oil layer was separated, and the aqueous phase was extracted with 50 cc additional xylene. The oil layer and extract were combined and distilled to give 82.4 g of unreacted 4-cyclohexylmethylpyridine (0.47 mole) and 9.0 g (0.03 mole) of 4,4'-di-(cyclohexylmethyl)-2,2'-bipyridyl boiling at 273°-276° C. at 2.5 mm Hg. The yield of 2,2'-bipyridyl product was calculated at 43.3% based on the amount of 4-cyclohexylmethylpyridine consumed. This 2,2'-bipyridyl compound (recrystallized from isopropanol) gave a melting point of 117°-119° C.

EXAMPLE 5

Experiment No. 15

4,4'-di-(4-tetrahydropyranyl)-2,2'-bipyridyl

In a one-liter, three-neck flask, equipped with a stirrer and dropping funnel, was prepared 0.22 moles of sodamide in liquid ammonia. The ammonia was replaced by adding 200 cc of xylene through the dropping funnel and applying heat to evaporate the ammonia. A thermometer and reflux condenser were attached to the flask, and the xylene mixture was brought to reflux. A solution of 200 g (1.23 mole) of 4-(4-tetrahydropyranyl)-pyridine dissolved in 200 g of xylene was added. The reaction mixture was refluxed at 138°-147° C. for 2 hours and hydrogen gas was given off. The flask was cooled to room temperature and hydrolyzed with 100 cc of water. The oil phase was separated and distilled to recover 179.5 g (1.10 mole) of 4-(4-tetrahydropyranyl)-pyridine and leave 10.4 g of residue. The residue was crystallized from acetone to give 5.3 g of 4,4'-di-(4-tetrahydropyranyl)-2,2'-bipyridyl with a melting point of 190°–192° C. The yield of 2,2'-bipyridyl product was calculated at 26.0%.

EXAMPLE 6

Experiment No. 16

4,4'-di-(3-phenylpropyl)-2,2'-bipyridyl

In a one-liter, three-neck flask was made 0.22 mole (5.0 g sodium) of sodamide in the usual way. The ammonia was replaced with 348 cc of xylene. The mixture was brought to reflux at 138° and 299.5 g (1.52 moles) of 4-(3-phenylpropyl)pyridine was added through a dropping funnel. Hydrogen evolution began immediately. Heating was continued for five hours at 138°–153° C. until hydrogen production slowed appreciably. The reaction mixture was cooled to around 100° C. and hydrolyzed with 100 cc of water. The oil layer was separated at room temperature and distilled through a Vigreaux column to give 182.5 g (0.93 moles) of unreacted 4-(3-phenylpropyl)pyridine and 62.9 g (0.16 mole) of 4,4'-di-(3-phenylpropyl)-2,2'-bipyridyl. The yield of 2,2'-bipyridyl product, based on 4-(3-phenylpropyl)-pyridine consumed, was 54.0%.

EXAMPLE 7

Experiment No. 18

4,4'-di-benzyl-2,2'-bipyridyl

One mole of sodamide was made in the usual way in liquid ammonia. The ammonia was replaced with 603.8 g (3.57 moles) of 4-benzylpyridine. The mixture was heated at 144°–218° C. for 26.5 hours. The light purple reaction mixture slowly gave off hydrogen with slowly increasing temperatures. The reaction mixture was cooled to about 100° C. and hydrolyzed with 75 cc of water. The oil layer was separated at room temperature. The aqueous layer was extracted with 50 cc of xylene. The oil layer and xylene extract were distilled through a Vigreaux distilling column to recover xylene and 515.0 g (3.05 moles) of unreacted 4-benzylpyridine. Further distillation gave 1.2 g (0.006 mole) of 2-amino-4-benzylpyridine (1.2% yield) and 52.7 g (0.16 mole) of 4,4'-di-benzyl-2,2'-bipyridyl with a melting point of 130°–132° C. The yield of 2,2'-bipyridyl product, based on 4-benzylpyridine consumed, was 59.7%.

EXAMPLE 8

Experiment No. 17

4,4'-di-(t-butyl)-2,2'-bipyridyl

In a one-liter, three-neck flask, equipped with a stirrer and dropping funnel, was prepared one mole of sodamide (23.0 g of sodium and iron catalyst) in 700 cc of liquid ammonia. The ammonia was replaced with 589.7 g (4.37 moles) of 4-t-butylpyridine. The mixture was heated to 135° C. at which time the purple reaction mixture began evolving hydrogen. The reaction was continued for 3.1 hours at 135°–149° C. until hydrogen evolution became slow. The reaction mixture was cooled to 100° C. and hydrolyzed with 100 cc of water. The oil layer was separated at 40° C. The aqueous layer was extracted with 50 cc of xylene. The oil layer and xylene extract were charged to a Vigreaux column for distillation. Xylene and about 300 g of unreacted 4-t-butylpyridine were distilled under vacuum. The residue was cooled to room temperature, allowing 4,4'-di-(t-butyl)-2,2'-bipyridyl to crystallize. It was filtered and washed with acetone to give 66.4 g of 4,4'-di-(t-butyl)-2,2'-bipyridyl with a melting point of 159°–160° C.

The filtrate was then further distilled to give more unreacted 4-t-butylpyridine and 57.7 g additional 2,2'-bipyridyl product (the boiling point of this 4,4'-di-(t-butyl)-2,2'-bipyridyl being about 235° C. at 32 mm Hg). The total 4-t-butylpyridine recovered was 448.7 g (3.32 moles). Yield of 4,4'-di-(t-butyl)-2,2'-bipyridyl, based on 4-t-butylpyridine consumed, was 88.7%. There was no evidence of any 2-amino-4-t-butylpyridine.

EXAMPLE 9

Experiment No. 19

6,6'-di-isoamyl-2,2'-bipyridyl

In a 300 cc, three-neck flask, equipped with a stirrer and dropping funnel, was made 0.2 mole of sodamide in liquid ammonia. The ammonia was replaced with 100 cc of xylene. A thermometer and reflux condenser were attached to the reaction flask, and the mixture was heated to reflux. Under reflux, 24.1 g (0.16 mole) of 2-isoamylpyridine was added from the dropping funnel. The reaction mixture turned to a deep purple and hydrogen began evolving. Refluxing was continued for 6.5 hours. The temperature range was 140°–146° C. At the end of the reflux, the reaction mixture was cooled to about 100° C. and hydrolyzed with 50 cc of water. The oil layer was separated at room temperature and the aqueous layer was extracted with 22 cc of xylene. The oil layer and xylene extract were distilled through a Vigreaux column to give 15.3 g of 2-isoamylpyridine (0.10 mole), 0.8 g of 2-amino-6-isoamylpyridine (8.2% yield) and 3.4 g of 6,6'-di-isoamyl-2,2'-bipyridyl (38.9% yield).

EXAMPLE 10

Following their preparation, the new substituted 2,2'-bipyridyl compounds of one embodiment of the present invention, as discussed above and listed in Tables I and II, were further tested and evidenced significant and valuable properties as chelating agents for various metal ions such as copper and iron. During this further testing, the new compounds also exhibited significant fungicidal and bactericidal properties.

TABLE I

| Experiment No. | 1 | 2 | 3 | 4 | 5 | 6 | 7 |
|---|---|---|---|---|---|---|---|
| Reagents | | | | | | | |
| Sodamide, grams | 19.5 | 39.0 | 39.0 | 19.5 | 8.6 | 11.8 | 39.0 |
| 4-(5-Nonyl) pyridine, grams | 102.5 | 102.5 | 205.0 | 205.0 | 500.0 | 200.0 | 250 |
| Mole Ratio Alkyl-pyridine/sodamide | 1.0 | 0.5 | 1.0 | 2.0 | 11.1 | 3.3 | 1.2 |
| Reaction Conditions | | | | | | | |
| Solvent | N,N (b) | N,N (b) | Xylene | Xylene | 4-(5-Nonyl) | Xylene | Xylene |

TABLE I-continued

| Experiment No. | 1 | 2 | 3 | 4 | 5 | 6 | 7 |
|---|---|---|---|---|---|---|---|
| | | | | | pyridine | | |
| Temperature °C. | 152–160 | 175–180 | 152–170 | 144–146 | 140–144 | 146–147 | 142–146 |
| Time, hours | 4 | 4.5 | 2.0 | 3.5 | 3.0 | 6 | 6 |
| Reaction Products | | | | | | | |
| Recovered 4-(5-Nonyl)pyridine, grams | 90.2 | 8.7 | 30.6 | 133.9 | 443.7 | 138.2 | 74.7 |
| 2-Amino-4-(5-Nonyl)pyridine, grams | 0 | 39.2 | 35.7 | 5.9 | 0 | 0 | 48.6 |
| % Yield (a) | 0 | 38.9 | 19.1 | 6.0 | 0 | 0 | 25.8 |
| 4,4'-Di-(5-Nonyl)-2,2'-Bipyridyl, grams | 0 | 18.6 | 82.2 | 69.6 | 41.8 | 50.0 | 86.6 |
| % Yield (a) | 0 | 19.9 | 47.4 | 76.8 | 74.6 | 81.3 | 49.6 |

(a) Yield is based on 4-(5-Nonyl)pyridine consumed.
(b) N,N-dimethylaniline

TABLE II

| Experiment No. | 8 | 9 | 10 | 11 | 12 | 13 |
|---|---|---|---|---|---|---|
| Reagents | | | | | | |
| Sodamide, grams | 7.8 | 19.5 | 7.8 | 19.5 | 7.8 | 7.8 |
| Alkylpyridine, | 2-(5-Nonyl)pyridine | 4-Isopropylpyridine | 4-(3-Pentyl)pyridine | 2-(3-Pentyl)pyridine | 2-(5-Nonyl)pyridine | 3-(5-Nonyl)pydridine |
| grams | 205.0 | 123.0 | 600.0 | 600.0 | 321.2 | 225.1 |
| Mole Ratio Alkylpyridine/Sodamide | 5.0 | 2.0 | 20.1 | 8.1 | 7.8 | 5.5 |
| Reaction Conditions | | | | | | |
| Solvent | N,N-dimethylaniline | Xylene | 4-(3-Pentyl)pyridine | 2-(3-Pentyl)pyridine | 2-(5-Nonyl)pyridine | 3-(5-Nonyl)pyridine |
| Temperature °C. | 197–198 | 140–141 | 140–147 | 178–180 | 188–198 | 164–175 |
| Time, hours | 3.0 | 5.3 | 8.9 | 11.5 | 26.2 | 15.0 |
| Reaction Products | | | | | | |
| Recover Alkylpyridine, grams | 125.0 | 94.8 | 531.5 | 420.4 | 235.3 | 138.4 |
| 2-Aminoalkylpyridine, grams | 2.3 | 0 | 0 | 0 | 0 | 0 |
| % Yield (a) | 2.7 | 0 | 0 | 0 | 0 | 0 |
| Substituted 2,2'-Bipyridyl, grams | 35.8 | 25.3 | 52.8 | 136.7 | 68.3 | 48.6 |
| % Yield (a) | 45.0 | 90.5 | 77.6 | 76.6 | 79.9 | 56.3 |

| Experiment No. | 14 | 15 | 16 | 17 | 18 | 19 |
|---|---|---|---|---|---|---|
| Reagents | | | | | | |
| Sodamide, grams | 3.9 | 8.5 | 8.5 | 39 | 39 | 7.8 |
| Alkylpyridine, | 4-Cyclohexylmethylpyridine | 4-(4-Tetrahydropyranyl)pyridine | 4-(3-Phenylpropyl)pyridine | 4-t-Butylpyridine | 4-Benzylpyridine | 2-Isoamylpyridine |
| grams | 103.3 | 200 | 299.5 | 589.7 | 603.8 | 24.1 |
| Mole Ration Alkylpyridine/Sodamide | 5.9 | 5.6 | 6.9 | 4.4 | 3.6 | 8.0 |
| Reaction Conditions | | | | | | |
| Solvent | Xylene | Xylene | Xylene | 4-t-Butylpyridine | 4-Benzylpyridine | Xylene |
| Temperature °C. | 128–148 | 138–147 | 138–153 | 135–149 | 144–218 | 140–146 |
| Time, hours | 3.5 | 2.0 | 5.0 | 3.1 | 26.5 | 6.5 |
| Reaction Products | | | | | | |
| Recovered Alkylpyridine, grams | 82.4 | 179.5 | 182.5 | 448.7 | 515.0 | 15.3 |
| 2-Aminoalkylpyridine, grams | 0 | 0 | 0 | 0 | 1.2 | 0.8 |
| % Yield (a) | 0 | 0 | 0 | 0 | 1.2 | 8.2 |
| Substituted 2,2'-Bipyridyl, grams | 9.0 | 5.3 | 62.9 | 124.1 | 52.7 | 3.4 |
| % Yield (a) | 43.3 | 26.0 | 54.0 | 88.7 | 59.7 | 38.9 |

(a) Yield is based on alkylpyridine consumed

What is claimed is:

1. A process for preparing a substituted 2,2'-bipyridyl compound, comprising the steps of:
   (a) selecting a singly-substituted alkylpyridine of the formula

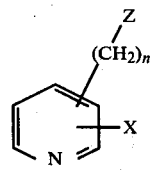

wherein:

(1) X is hydrogen or an alkyl group having from 1 to about 9 carbon atoms;
(2) Z is:
  (i) a branched chain alkyl group having from 3 to about 20 carbon atoms connecting to $(CH_2)_n$ at a point of branching when n=0, 1, 2; or
  (ii) a cyclic structure of the type

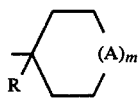

when n=0, 1, 2, wherein
  (a) A is methylene, oxygen, or sulfur when m=0, 1; and
  (b) R is hydrogen or an alkyl group having from 1 to about 4 carbon atoms; or
  (iii) a phenyl group when n=1, 2, 3,; and
(3) the 2- or 6-position is occupied by hydrogen; and
(b) mixing a stoichiometric excess of the substituted pyridine with an amount of sodamide, said mixing being in a mole ratio of at least about 2:1;
(c) causing the resultant mixture to be at a temperature sufficiently high to cause substituted 2,2'-bipyridyl formation; and
(d) isolating the substituted 2,2'-bipyridyl formed during said causing.

2. The process of claim 1 in which said selecting is of a substituted pyridine from the group consisting of:
4-(5-nonyl)pyridine;
4-isopropylpyridine;
4-(3-pentyl)pyridine;
2-(3-pentyl)pyridine;
2-(5-nonyl)pyridine;
4-cyclohexylmethylpyridine;
3-(5-nonyl)pyridine;
4-(4-tetrahydropyranyl)pyridine;
4-(3-phenylpropyl)pyridine;
4-t-butylpyridine;
4-benzylpyridine; and
2-isoamylpyridine.

3. The process of claim 2 in which said selecting is of 4-(5-nonyl)pyridine.

4. The process of claim 1 in which said causing is for a period of time sufficient to provide a yield of at least about 50 percent.

5. The process of claim 1 additionally comprising refluxing the resultant mixture after said mixing and during said causing.

6. The process of claim 1 in which said mixing is in the mole ratio of at least about 3:1.

7. The process of claim 6 in which said causing is for a period of time sufficient to provide a yield of at least about 50 percent.

8. The process of claim 7 in which said isolating comprises distilling off the substituted 2,2'-bipyridyl from the resultant mixture.

9. The process of claim 8 in which said isolating additionally comprises recovering and recycling the unreacted substituted pyridine.

10. The process of claim 6 in which said causing is to a temperature of between about 140° C. and about 220° C.

11. The process of claim 10 in which said causing is for a period of at least about 3 hours.

12. The process of claim 11 additionally comprising refluxing the resultant mixture during said causing.

13. The process of claim 12 in which said isolating comprises distilling off the substituted 2,2'-bipyridyl from the resultant mixture.

14. The process of claim 13 in which said isolating additionally comprises recovering and recycling the unreacted substituted pyridine.

15. The process of claim 14 in which said selecting is of a substituted pyridine from the group consisting of:
4-(5-nonyl)pyridine;
4-isopropylpyridine;
4-(3-pentyl)pyridine;
2-(3-pentyl)pyridine;
2-(5-nonyl)pyridine;
4-cyclohexylmethylpyridine;
3-(5-nonyl)pyridine;
4-(4-tetrahydropyranyl)pyridine;
4-(3-phenylpropyl)pyridine;
4-t-butylpyridine;
4-benzylpyridine; and
2-isoamylpyridine.

16. The process of claim 15 in which said selecting is of 4-(5-nonyl)pyridine.

17. The process of claim 14 in which said causing is in the presence of a hydrocarbon solvent.

18. The process of claim 17 in which the hydrocarbon solvent is xylene.

* * * * *